United States Patent [19]
Roline et al.

[11] Patent Number: 5,312,454
[45] Date of Patent: May 17, 1994

[54] APPARATUS AND METHOD OF AUTOMATICALLY ADJUSTING A SENSOR SIGNAL COMPARATOR THRESHOLD FOR AN OXYGEN SENSING PACEMAKER

[75] Inventors: Glenn M. Roline, Anoka; Dennis A. Brumwell, Bloomington, both of Minn.

[73] Assignee: Medtronic, Inc., Minneapolis, Minn.

[21] Appl. No.: 947,859

[22] Filed: Dec. 14, 1992

[51] Int. Cl.$^5$ ............................................. A61N 1/36
[52] U.S. Cl. ...................................... 607/22; 607/28; 128/633; 128/664; 128/665; 128/666
[58] Field of Search .................... 607/9, 17, 18, 22, 28; 128/633, 634, 664, 665, 666, 667

[56] References Cited

U.S. PATENT DOCUMENTS

| | | | |
|---|---|---|---|
| 4,523,279 | 6/1985 | Sperinde et al. | 128/666 |
| 4,750,495 | 6/1988 | Moore et al. | 128/419 |
| 4,813,421 | 3/1989 | Baudino et al. | 607/22 |
| 4,903,701 | 2/1990 | Moore et al. | 128/419 |

Primary Examiner—William E. Kamm
Assistant Examiner—Kennedy J. Schaetzle
Attorney, Agent, or Firm—Dwight N. Holmbo; Harold R. Patton

[57] ABSTRACT

A monitoring system for an oxygen sensing, dual-wavelength, reflectance oximetry based, rate responsive cardiac pacemaker, is capable of automatically and continually adjusting an oxygen sensor signal comparator threshold such that the effects of noise, sensitivity and drift on oximeter output signals sent to the pacemaker are minimized. A comparator and related circuitry are configured to sample and compare supply excitations for multiple oxygen sensor light sources. The comparator threshold is adjusted as a function of supply excitation for each light source independently of one another, thereby providing an oxygen sensing pacemaker with optimal noise immunity since one of the more vulnerable portions of the pacing system is the transfer of the light source signals which are susceptible to noise.

7 Claims, 8 Drawing Sheets

APPARATUS AND METHOD OF AUTOMATICALLY ADJUSTING A SENSOR SIGNAL COMPARATOR THRESHOLD FOR AN OXYGEN SENSING PACEMAKER

FIELD OF THE INVENTION

The present invention relates to cardiac pacing generally and in particular to an oxygen sensing pacemaker which automatically adjusts the threshold of a dual-wavelength oximeter signal comparator for increased noise immunity.

BACKGROUND OF THE INVENTION

Rate responsive cardiac pacemakers which measure a physiologic parameter indicative of metabolic demand and vary the pacing rate as a function thereof are well-known. The relationship between a parameter such as oxygen saturation of the blood and a patient's corresponding metabolic demand and desired heart rate is also well-known. Consequently, pacemakers which regulate pacing rate in response to sensed blood oxygen level and attempt to restore the desired relationship between blood oxygen level and pulse rate in order to meet a patient's physiological demands are believed particularly desirable for individuals requiring rate responsive pacemaker support.

A thorough description of demand pacemakers having such oxygen-sensing capabilities utilizing dual-wavelength, reflectance oximetry technology can be found, for example, in U.S. Pat. No. 4,903,701, issued to Moore et al., as well as in U.S. Pat. No. 4,750,495, issued to Moore et al.

While the performance of such prior devices has been generally acceptable, some concern exists that there may be undesired susceptibility to noise riding upon the signal being monitored. The problem presents itself when attempting to balance the need for maintaining adequate signal sensitivity (i.e., by setting the comparator threshold of the sensor signal comparator sufficiently "close to" the expected signal amplitude levels expected to be sensed to promptly detect appropriate signal level transitions) with the need of maintaining adequate noise immunity (i.e., by setting the comparator threshold of the sensor signal comparator sufficiently "far away from" the expected signal amplitude levels expected, together with noise riding thereon, to avoid inappropriate detection by the comparator).

Another problem is the extent to which the sensitivity of such sensor-based devices may vary from unit to unit, unless each unit's comparator threshold has been uniquely established at an amplitude which is appropriate for the particular sensor signal amplitudes generated by that particular unit's sensor circuitry.

A further problem can develop, for example, with respect to the same unit over time due to aging effects upon critical optical components required to produce light emissions and sense reflected light, such that the signal amplitudes generated by such unit may drift to an unacceptable extent with respect to what is typically a relatively fixed-level comparator threshold.

Therefore, what is needed is a monitoring system for such devices, particularly such as for the subject oxygen-sensing, dual-wavelength, reflectance oximetry based, rate responsive cardiac pacemaker disclosed herein, wherein continual and automatic adjustments are made by the monitoring system to the sensor signal comparator threshold, such that the effects of noise, sensitivity and drift on oximeter output signals sent to the pacemaker are minimized.

SUMMARY OF THE INVENTION

The present invention provides a refined version of an oxygen sensing pacemaker. That portion of the pacemaker which compares the output signals from the oximeter light sources provides optimal noise immunity by automatically adjusting the comparator signal sensing threshold during the comparing process. Experience in the field of oxygen sensing cardiac pacing has shown that one of the more vulnerable portions of the pacing system is the transfer of the light source signals, which is susceptible to noise to the pacemaker. Therefore, it is felt that adjusting the light source signal comparator threshold independently for each light source will enhance the pacemaker noise immunity while increasing the reliability and accuracy of rate response as a function of sensed blood oxygen level.

The comparator and related circuitry are configured to sample and compare supply excitations for two sensor light sources. The sensor in the preferred embodiment includes an oscillator which sequentially activates red and infrared diodes. The activation times of the infrared and red diodes are determined by the amounts of infrared and red light reflected by the blood. The sensor requires substantially more excitation when the red light source is activated than when the infrared light source is activated. This allows the pacemaker to measure the durations of the red and infrared light source activation periods. Thus, adjusting the comparator threshold as a function of supply excitation for each light source independent of each other will provide an oxygen sensing pacemaker with optimal noise immunity.

DETAILED DESCRIPTION OF THE DRAWINGS

Figure 1:
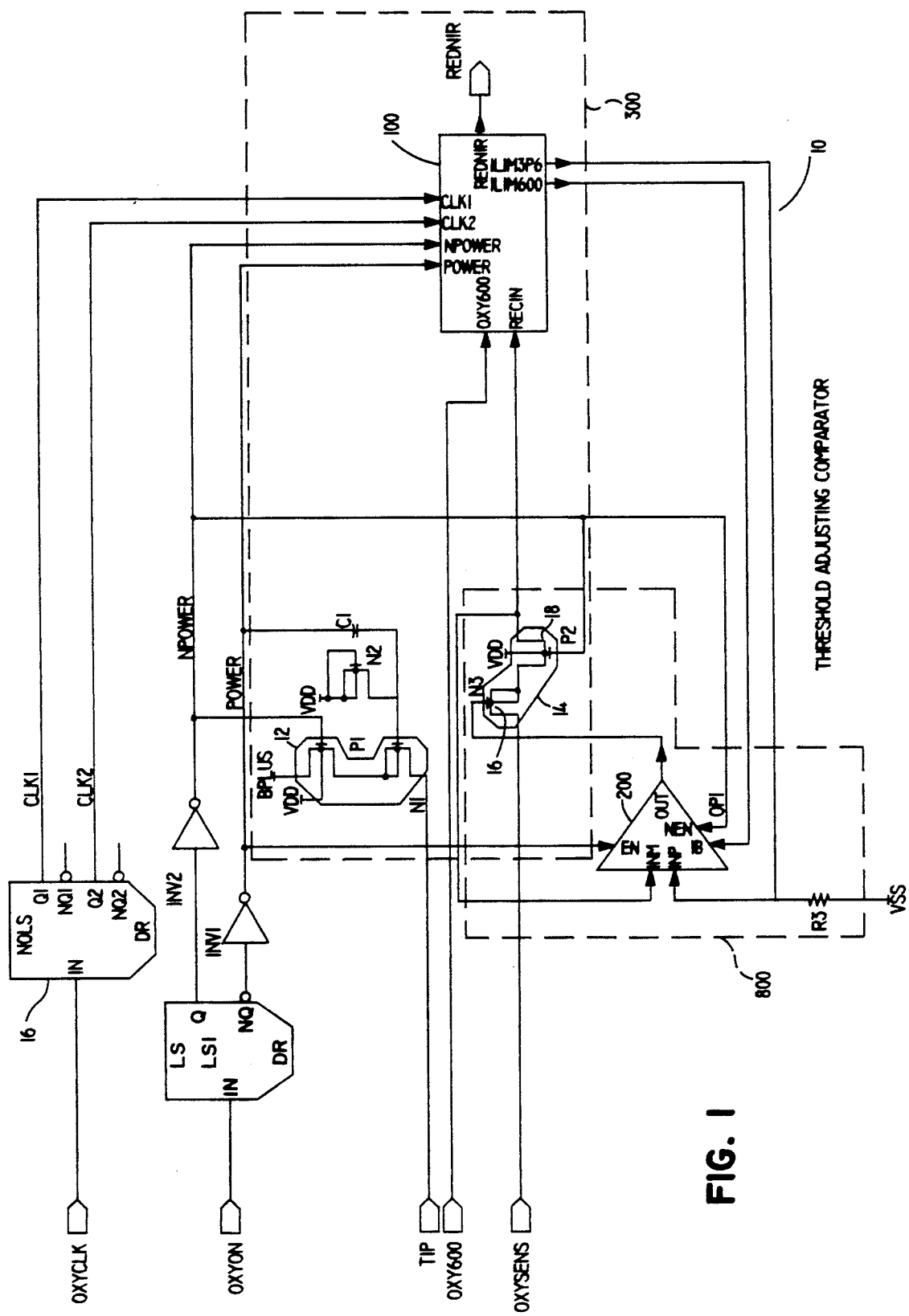
FIG. 1 is a detailed schematic of the preferred embodiment for the threshold adjusting comparator and associated circuitry within the pacemaker.
Figure 2:
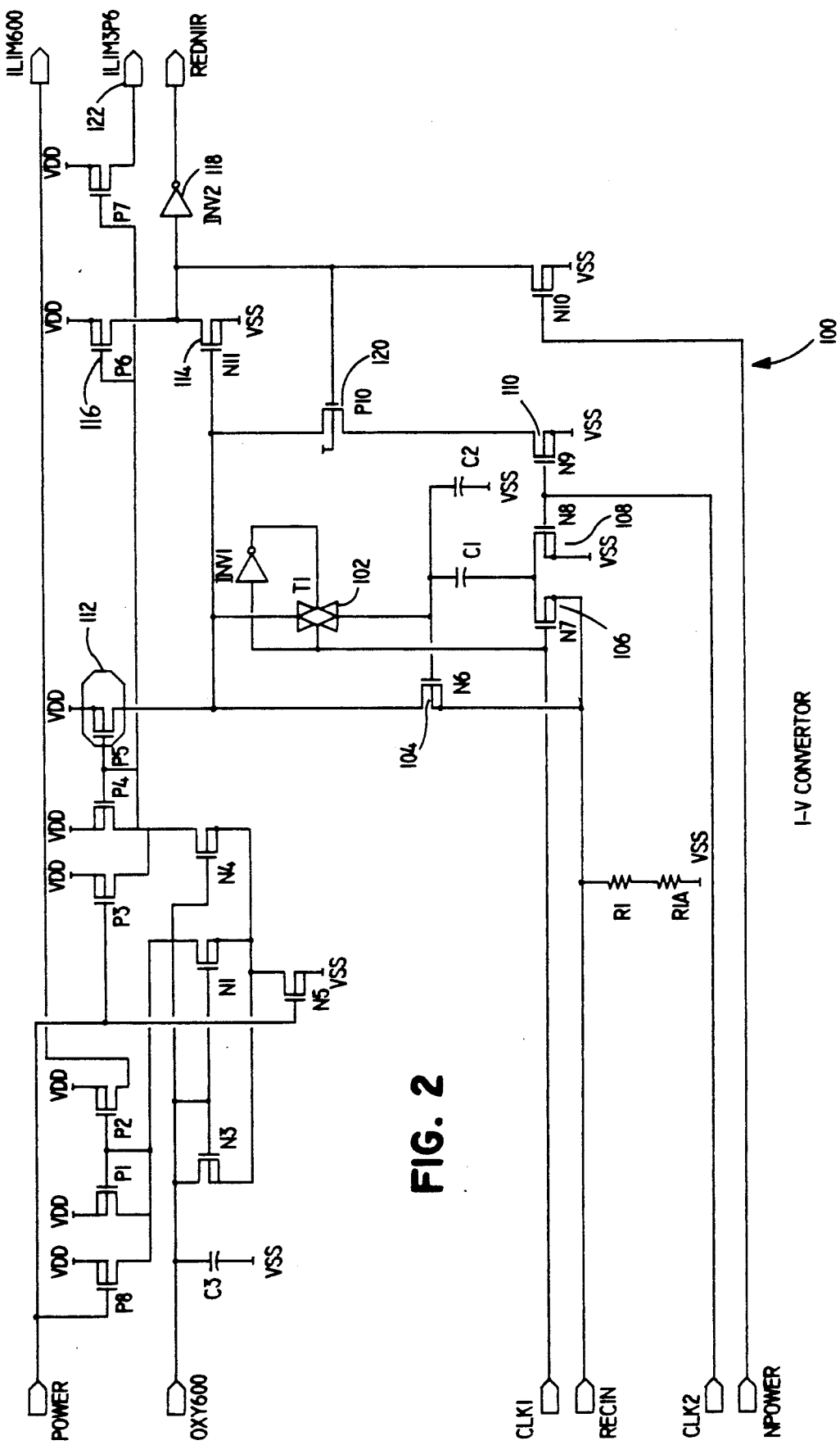
FIG. 2 is a detailed schematic of a portion of the preferred embodiment of FIG. 1 further illustrating associated logic and current-voltage conversion circuitry.
Figure 3:
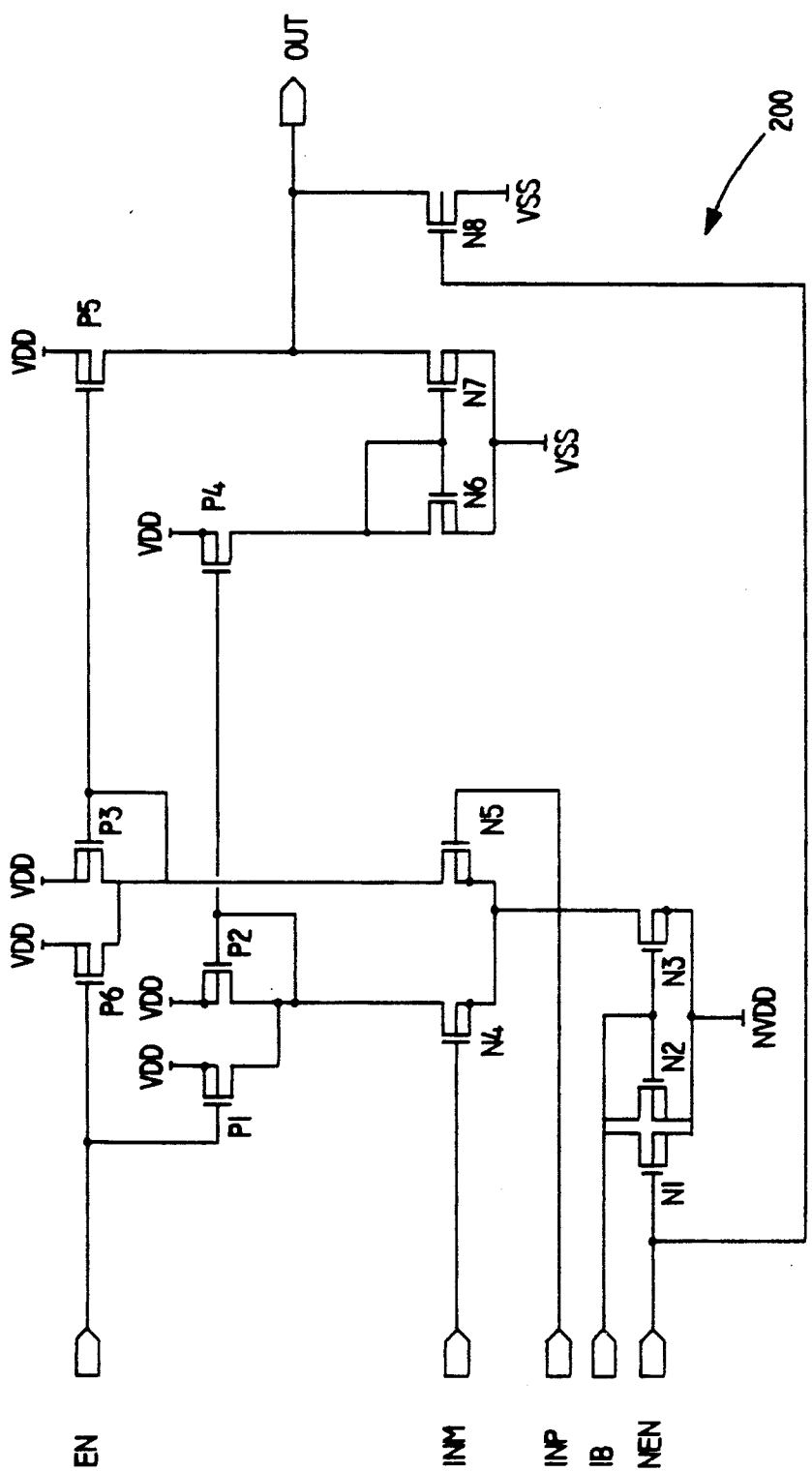
FIG. 3 is a detailed schematic of a portion of the preferred embodiment of FIG. 1 further illustrating additional sensor excitation limiter circuitry.

The preferred embodiment for the threshold adjusting comparator circuit is unique in that it converts the oxygen sensor light source derived excitation pulses to logic signals and automatically adjusts the comparator threshold to a midpoint between two light source excitation levels. The operation of the comparator circuit in FIGS. 1 and 2 will be explained via the simplified circuits illustrated in FIGS. 4 through 8. FIG. 3 is a standard operational amplifier design and will not be described herein.

Figure 4:
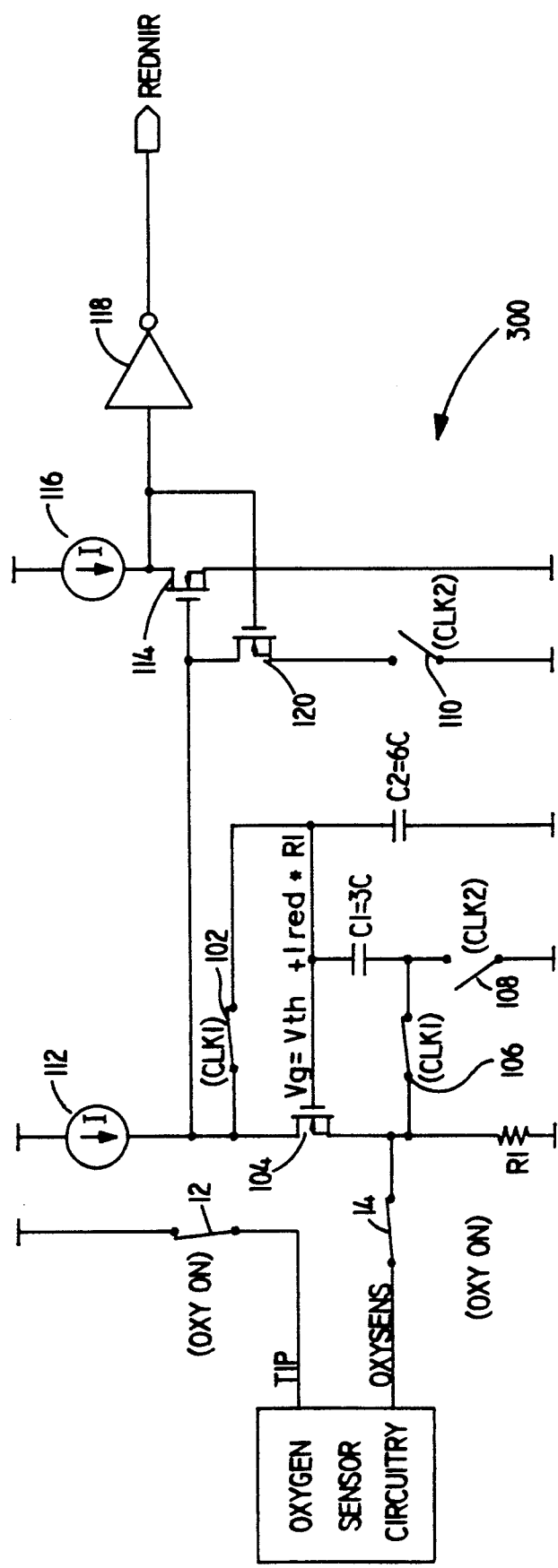
FIG. 4 is a simplified version of the preferred embodiment of FIG. 1 illustrating operation of the threshold adjusting comparator during the sampling period.
Figure 5:
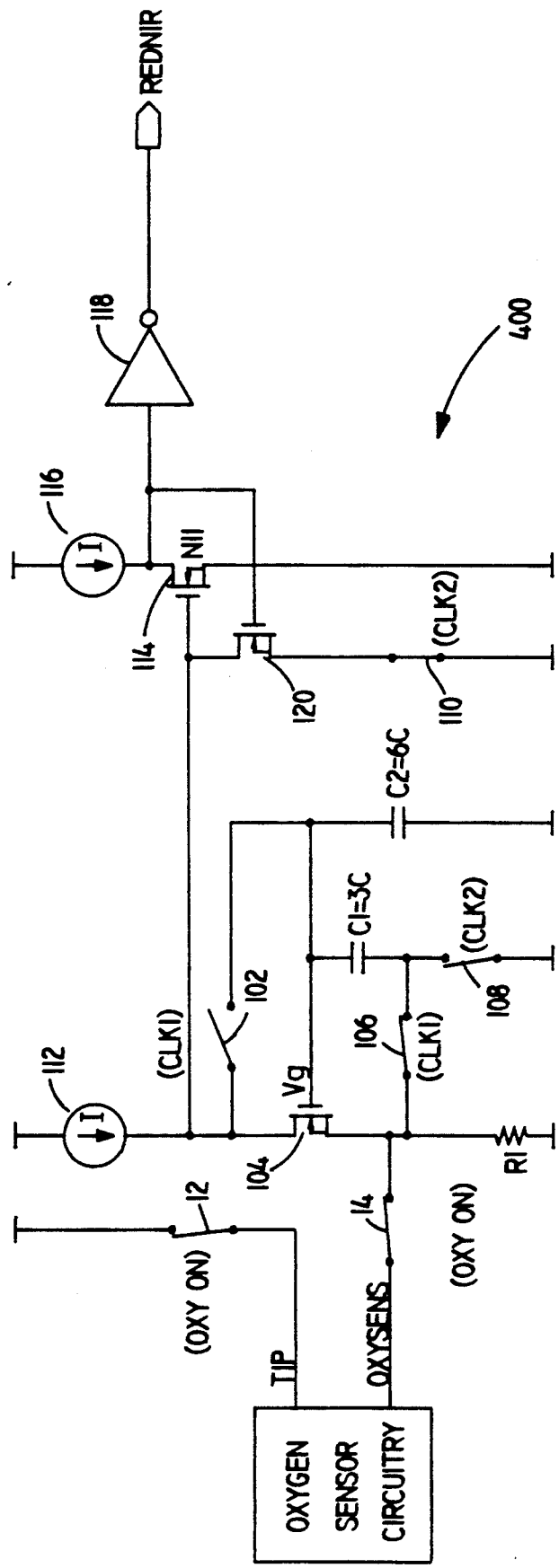
FIG. 5 is a simplified version of the preferred embodiment of FIG. 1 illustrating operation of the threshold adjusting comparator during the compare period.
Figure 6:
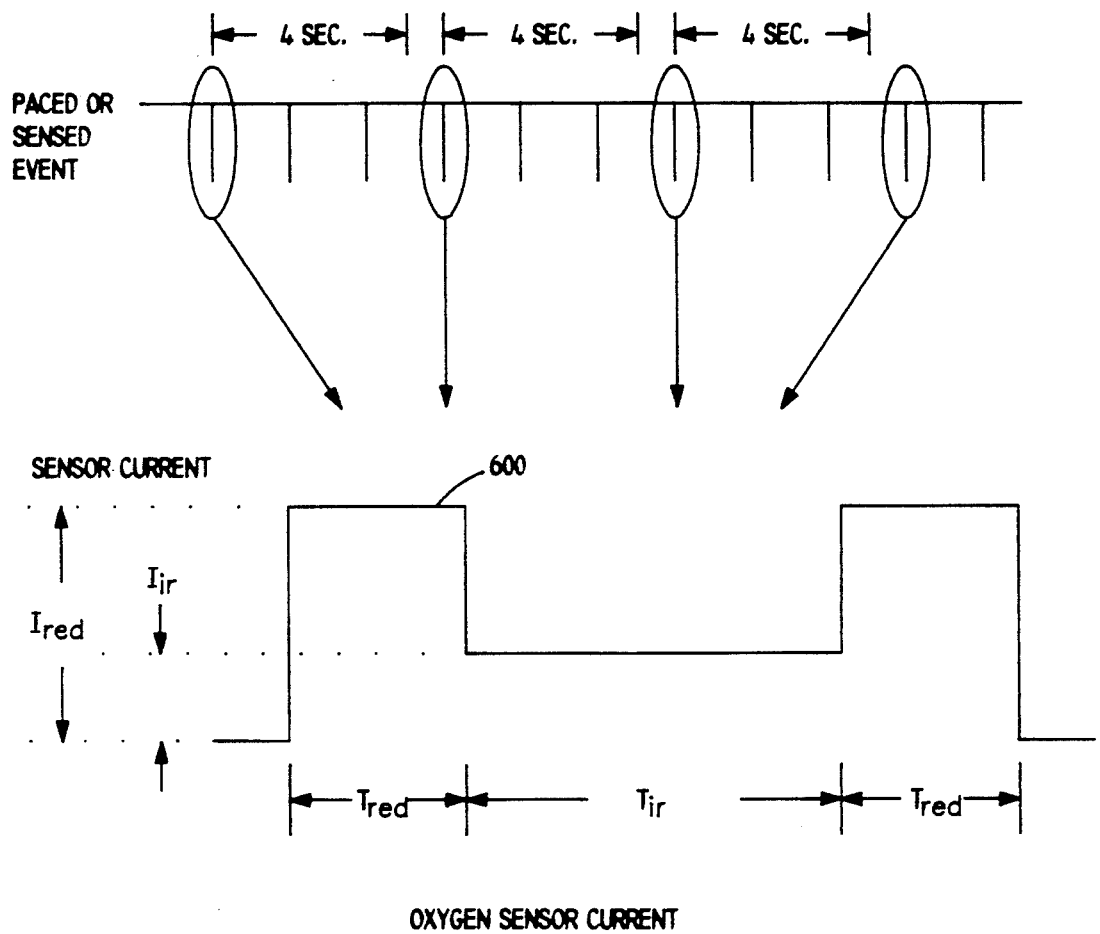
FIG. 6 is a timing diagram for the preferred embodiment illustrating the light source supply excitation current pulses following a sensed or paced event subsequent to a four second time-out.

In FIG. 4, the comparator logic signal labeled OXYON applies power to the oxygen sensor light sources through FET Switches 12 and 14 following a sensed or paced event after a four second time-out as shown in FIG. 6. Switch 12 in FIG. 4 applies the positive power source while switch 14 applies the negative power source and couples the sensor light source signals to the current to voltage converter 100 in FIG. 1. Switches 12 and 14 are a series N and P channel MOS FET to form a complementary pair to block input signals that exceed the supply excitation, such as cautery and defibrillation signals. The sensor light source current 600 as illustrated in FIG. 6 passes through resistor R1 shown in FIGS. 2, 4 and 5 which converts the current pulses to the input voltage pulses 700 illustrated in FIG. 7.

There are two phases to the operation of the preferred embodiment; the sampling phase as illustrated in FIG. 4, and the compare phase as illustrated in FIG. 5. The logic signal labeled OXYCLK, in conjunction with the non-over lapping clock generator 16 in FIG. 1, controls the timing of the two phases labeled CLK1 and CLK2 in FIGS. 1, 2, 4 and 5.

The sampling phase (CLK1 in FIG. 7) starts at the initiation of power (OXYON in FIG. 7) to the oxygen sensor and lasts from 244 to 488 μsec. During the sampling phase, the oxygen sensor is expected to be in its power up condition wherein the RED LED is on. During the sampling phase, switch 102 is closed, connecting the drain of FET 104 to its gate, thus forcing the FET 104 drain potential to be at the threshold level of FET 104. Switch 106 is also closed, thereby connecting the bottom of capacitor C1 to the source connection of FET 104, thus causing the storage of the FET 104 threshold voltage onto C1. The voltage stored on C2 in this condition is the FET 104 threshold voltage plus the voltage drop developed across R1 due to the RED LED current flowing through R1. Switch 108 (FET N8) and 110 (FET N9) are open during the sampling phase.

During the transition to the compare phase switch 102 and 106 open just prior to the closing of switch 108 and 110, thus not disturbing the stored charge on C1 and C2. The opening of Switch 102 places FET 104 into a common gate configuration. The closing of Switch 108 causes the charge stored in C1 and C2 to redistribute.

During the sampling phase, the charge stored onto the capacitors C1 and C2 is:

$$Q_{C1} = V_{th} * 3C \qquad 1.1$$

$$Q_{C2} = (V_{th} + I_{red} * R1) * 6C \qquad 1.2$$

During the compare phase, the charge redistributes and the result is $V_g$:

Due to charge conservation $$Q_{(C1+C2)} = Q_{C1} + Q_{C2} \qquad 2.1$$

and $$Q_{(C1+C2)} = V_g * (3C + 6C) \qquad 2.2$$

Solving for FET 104 gate voltage by substituting equations 1.1, 1.2 and 2.2 into equation 2.1, the resulting $V_g$ is:

$$V_g = V_{th} + (\tfrac{2}{3}) * I_{red} * R1 \qquad 2.3$$

Solving for the input threshold by subtracting the threshold of FET 104:

$$V_{threshold} = (\tfrac{2}{3}) I_{red} * R1 \qquad 3.1$$

Where:
 $V_g$ = Voltage present at the gate of FET 104 during the compare phase,
 $V_{th}$ = Threshold voltage of FET 104,
 $I_{red}$ = Current level of sensor when RED LED is on and during sample phase,
 C = Unit Capacitor, and
 R1 = Value of resistor R1.

Figure 7:
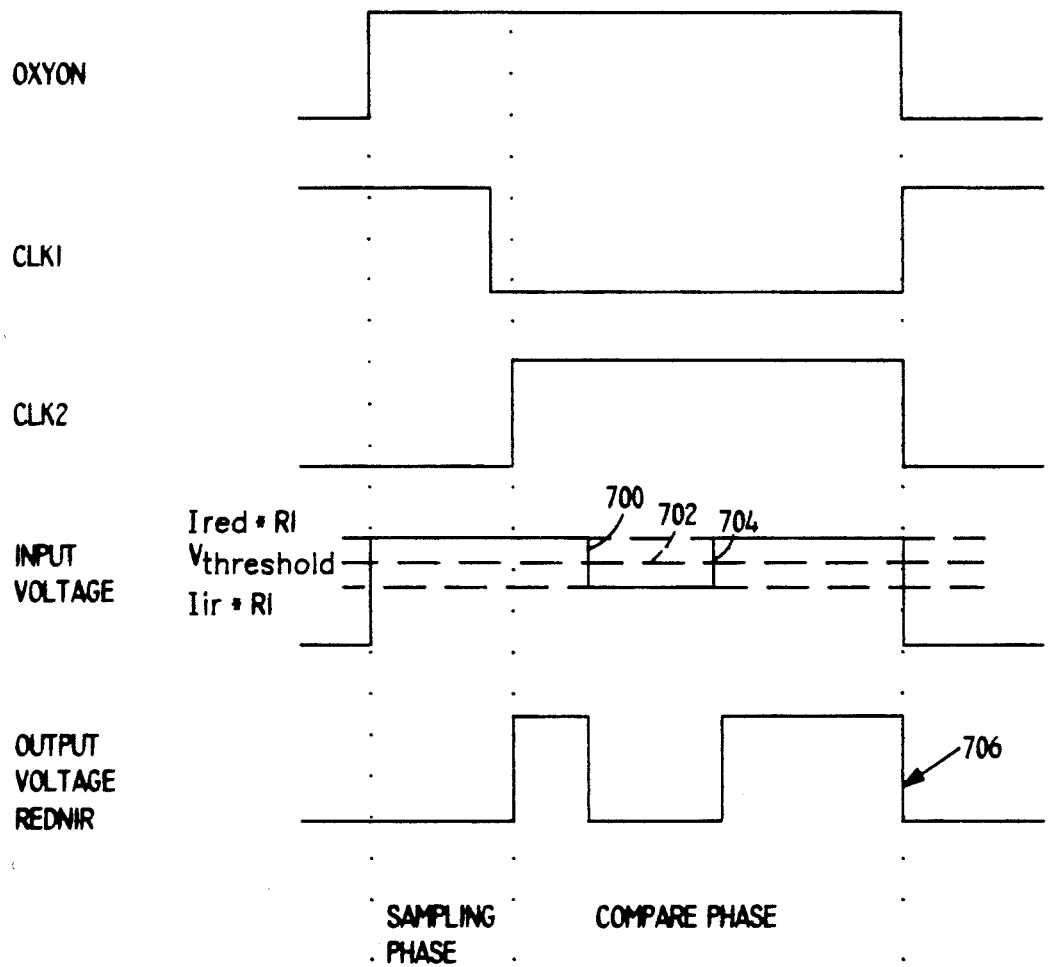
FIG. 7 is a timing diagram for the preferred embodiment illustrating conversion of the excitation current pulses in FIG. 6 to output voltage pulses, thereby providing a duty-modulated output signal.

Moving now to FIG. 7, a duty-cycle modulated sensor signal is illustrated, wherein the signal transitions from a first signal amplitude (corresponding to $I_{ir}*R1$) to that of a second signal amplitude (corresponding to $I_{red}*R1$), and the sensor signal comparator threshold which is being adjustably maintained at a predetermined amplitude therebetween on a cycle-to cycle basis (corresponding to $V_{threshold}$ which is held at midpoint).

It can be seen that a current level change, such as when the $I_{ir}$ LED turns on 700, causes the voltage drop across R1 to decrease below the $V_{threshold}$ voltage 702, thereby causing FET 104 to turn on. This causes the drain voltage of FET 104 to move negative turning off FET Switch 114. FET Switch 114 again amplifies and inverts this transition which causes the output signal (REDNIR) of invertor 118 to transition low.

Whenever the current level of the oxygen sensor causes the voltage drop across R1 to exceed the threshold voltage ($V_{threshold}$) determined by Equation 3.1, FET 104 will turn off and the current source 112 will cause the drain of FET 104 to move positive thereby turning on Switch 114 (FET N11). Switch 114 in conjunction with the current source load 116 amplifies and inverts this transition thereby causing the output signal (REDNIR) of invertor 118 to transition high, as indicated at 704. FET 120, which was activated when Switch 110 closed, clamps the drain of FET 104 at the threshold level of FET 120. This prevents the occurrence of a large voltage swing at the drain of FET 104, thus reducing the transition time at this node. As indicated at transition 706, output voltage (REDNIR) transitions low and the corresponding pacemaker logic turns off power to oxygen sensor (OXYON).

Since the threshold of the comparator circuit automatically adjusts itself to ⅔ the current level of the RED LED, the magnitude of the current levels can vary considerably from sensor to sensor and not effect the recovery of the sensor signal. The only requirement is that the change in current must exceed ⅓ of the RED LED current level. In the preferred embodiment, the IR LED current level is set at ⅓ that of the RED LED current level, thus causing a current level change of ⅔ the RED LED current level. In the preferred embodiment, the ratio between the two current levels is tightly controlled due to IC component matching characteristics. This concept has eliminated the need for a trimmed sensor current level.

Figure 8:
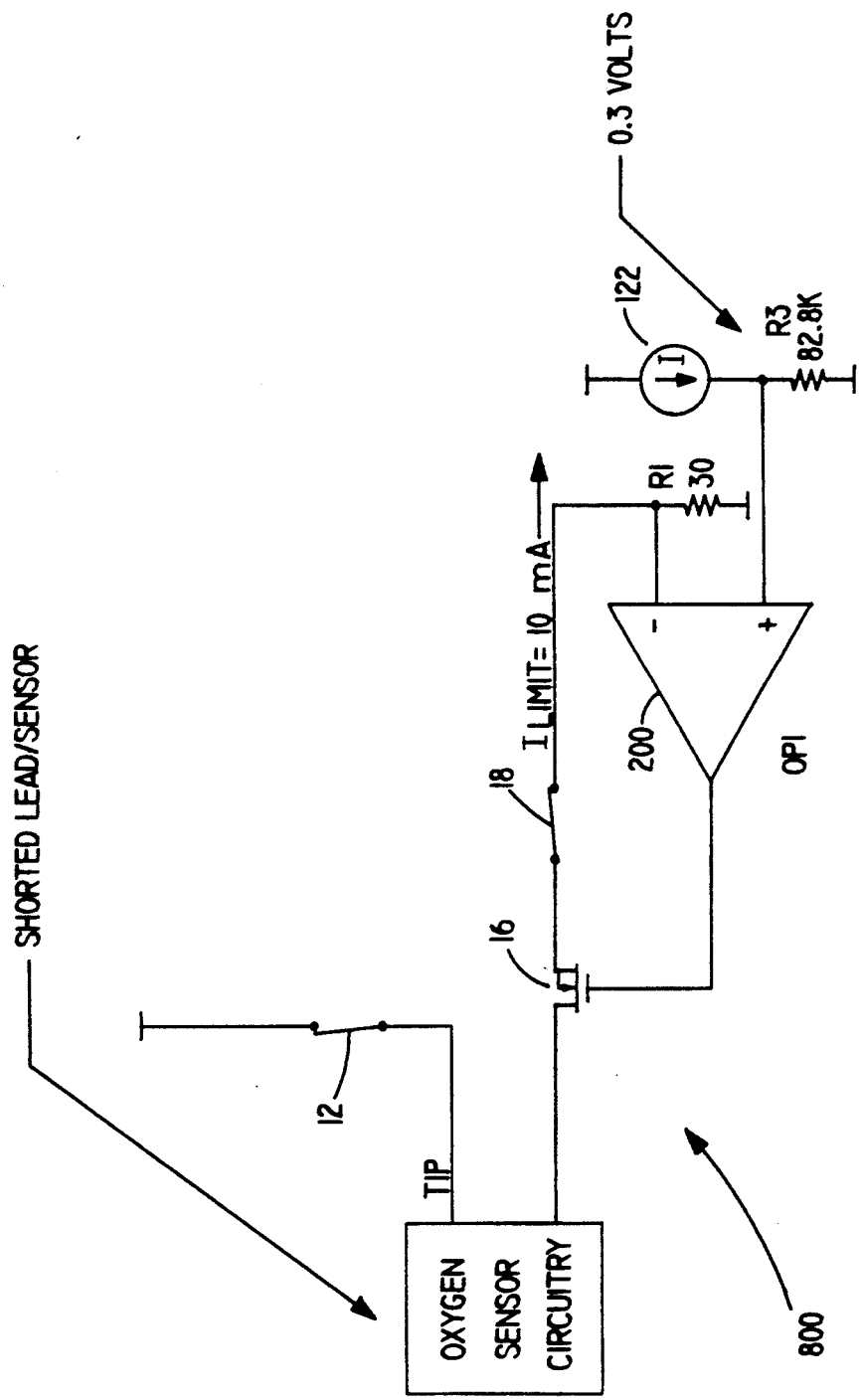
FIG. 8 is a simplified version of a portion of the preferred embodiment illustrating operation of the current limiter circuitry.

FIG. 8 illustrates a portion of the preferred embodiment for the threshold adjusting comparator illustrating a current limiter 800. In the event of a short in the pacemaker lead or connector system, this current limiter 800 prevents large battery current spikes which could cause the pacing system to operate unpredictably. This circuit 800 consists of the operational amplifier 200, resistor R3, FET 16 and resistor R1. The operation of circuit 800 will be explained hereinafter.

A current source 122 causes a current labeled ILIM3P6 to flow through resistor R3, setting up a fairly stable voltage source at the positive input of operational amplifier 200. The sensor is powered on by closing Switches 12 and 18 and turning FET 16 on. The sensor current flows through these devices and through R1. The current flowing through R1 creates a voltage source at the negative input of operational amplifier 200 whose value is dependent on the oxygen sensor current. Under normal operating conditions, the current flow is low thus creating a voltage drop across R1 that is less than the voltage drop across R3. This situation causes the operational amplifier 200 output to be high and thereby fully turn on FET 16. In a condition where a short might exist, the current level through R1 increases until it is equal to the voltage drop across R3. At this point, the operational amplifier 200 output starts to decrease which starts to limit and regulate, via the feedback path through FET 16 to the negative input of operational amplifier 200, the current flow through FET 16, the sensor, lead, connector system and R1. The current level in which this limiting effect occurs can be described by the following equation:

$$I_{LIMIT} = I_{LIM3P6} * (R3/R1).$$

While the invention has been described above in connection with a particular embodiment, one skilled in the art will appreciate that the invention is not necessarily so limited. It will thus be understood that numerous other embodiments, examples, uses, modifications of, and departures from the teachings disclosed may be made, without departing from the scope of the present invention as claimed herein.

For example, it will be readily understood by those skilled in the art that the subject invention can be practiced using a sensor which monitors parameters other than oxygen, including without limitation, pressure, temperature, flow and others, in which the sensor provides a duty-cycle modulated signal. It will also be understood that the modulated signals to which the comparator threshold is being adjustably maintained need not constitute a power signal, but can also comprise the sensor's output signal in general.

What I claim is:

1. A rate responsive cardiac pacemaker which varies its pacing rate at controlled intervals as a function of a sensed physiologic parameter for use with a cardiac pacing electrode for applying said pacing pulses to the heart, comprising:

(a) sensor means for measuring said physiologic parameter and for generating a sensor signal indicative thereof;
   (b) power supply means for supplying a power signal to excite said sensor means, wherein said sensor means modulates said power signal supplied to said sensor means such that said modulated power signal comprises said sensor signal, said sensor signal being duty-cycle modulated between a first amplitude for a first time period and a second amplitude for a second time period, said second amplitude being greater than said first amplitude;
   (c) monitoring means for monitoring said modulated sensor signal and for determining the relative durations of said first and second signal amplitudes, said monitoring means including signal comparator means having a signal threshold value between said first and second signal amplitudes, said signal comparator means for comparing said modulated signal amplitudes with said threshold value and providing a demodulated signal representative of such measured physiological parameter, said comparator means further including means for measuring at least one of said first and second amplitudes and for automatically adjusting said threshold value as a function of at least one of said first and second amplitudes; and
   (d) rate responsive means for varying said cardiac pacing rate as a function of said demodulated signal.

2. A rate responsive pacemaker according to claim 1, wherein said physiological parameter comprises blood oxygen levels and wherein:
   (a) said sensor means comprises a dual-wavelength, reflectance oximeter, said sensor means further including:
      (1) oscillator means for sequentially activating said dual-wavelength oximeter, thereby activating a first wavelength light source for a first activation period and a second wavelength light source for a second activation period;
      (2) means for allowing said light provided by said first and second wavelength light sources to impinge upon the blood and for allowing said light reflected by said blood to reenter said sensor means;
      (3) light sensing means for sensing said light of said first and second wavelengths and for regulating said first and second activation periods dependent upon the amount of light reflected by said blood; and
   (b) said power supply means modulates said power signal in accordance with said first and second activation periods.

3. A rate responsive pacemaker according to claim 2, wherein said first and second light wavelengths comprise infrared and red.

4. A method of automatically adjusting a comparator threshold of a sensor signal comparator for a rate responsive pacemaker which varies its pacing rate at controlled intervals as a function of a sensed physiological parameter, wherein said sensor signal comprises a duty-cycle modulated signal which varies between a first amplitude for a first time period and a second amplitude for a second time period as a function of said parameter being sensed, said second amplitude being greater than said first amplitude, and wherein said pacing rate is varied as a function of the relative durations of said signal amplitudes which are detected by said sensor signal comparator with respect to said threshold, the method comprising the steps of:

(a) measuring at least one of said first and second signal amplitudes on a recurring signal cycle basis; and (b) adjusting said threshold to a desired threshold amplitude which is between said first and second amplitudes, said threshold amplitude being adjusted on a recurring signal cycle basis such that said threshold amplitude comprises a predetermined function of said measured amplitudes.

5. A method of automatically adjusting a comparator threshold of a sensor signal comparator according to claim 4, wherein:

(a) step (a) thereof comprises measuring said second amplitude; and (b) step (b) thereof comprises adjustably maintaining said threshold amplitude at a predetermined percentage of said measured second amplitude.

6. A method of automatically adjusting a comparator threshold of a sensor signal comparator according to claim 4, wherein:

(a) step (a) thereof comprises measuring said first and second amplitudes; and (b) step (b) thereof comprises adjustably maintaining said threshold amplitude at a predetermined percentage of the amplitude range defined between said measured first and second amplitudes.

7. A method of automatically adjusting a comparator threshold of a sensor signal comparator according to claim 6, wherein said predetermined amplitude level is substantially midpoint between said measured first and second amplitudes.

* * * * *